United States Patent [19]

Iki et al.

[11] Patent Number: 5,691,800
[45] Date of Patent: Nov. 25, 1997

[54] OPHTHALMOLOGIC APPARATUS

[75] Inventors: Yoichi Iki; Seiho Yamashita, both of Kawasaki, Japan

[73] Assignee: Nikon Corporation, Tokyo, Japan

[21] Appl. No.: 580,991

[22] Filed: Jan. 3, 1996

[30] Foreign Application Priority Data

Jan. 23, 1995 [JP] Japan ............................ 7-008376

[51] Int. Cl.$^6$ ............................................. A61B 3/10
[52] U.S. Cl. ............................................. 351/212; 351/205
[58] Field of Search ................................. 351/211, 212, 351/221, 208, 205, 200, 246, 247

[56] References Cited

U.S. PATENT DOCUMENTS 4,390,255  6/1983  Nohda et al. ............................ 351/212

FOREIGN PATENT DOCUMENTS

| 29 37 891 | 4/1980 | Germany . |
| 55-52730 | 4/1980 | Japan . |
| 5-66125 | 9/1993 | Japan . |

OTHER PUBLICATIONS

Patent Abstracts of Japan, vol. 18, No. 187 (P–1720), Mar. 30, 1994 (JP–A–5 346371).

*Primary Examiner*—Hung X. Dang
*Attorney, Agent, or Firm*—Shapiro and Shapiro

[57] ABSTRACT

An ophthalmologic apparatus comprises a measuring device for measuring an eye being examined, a display for displaying the result of the measurement by the measuring device, a counter for counting the number of times of measurement of the eye being examined with respect to each of the right and left eyes, and a display control device for causing the display to display the number of times of measurement of each of the right and left eyes counted by the counter.

6 Claims, 6 Drawing Sheets

PATIENT

PATIENT

OPERATOR  MONITOR  APPARATUS  PATIENT

OPHTHALMOLOGIC APPARATUS

BACKGROUND OF THE INVENTION

1. Field of the Invention

This invention relates to an ophthalmologic apparatus such as an auto-refractometer, a keratometer for measuring corneal curvature or a tonometer for measuring intraocular pressure.

2. Related Background Art

In many of ophthalmologic apparatuses as mentioned above, measurement is effected about one eye of a patient a plurality of times, whereafter similar measurement is effected about the other eye a plurality of times, and a measurement result of good accuracy is extracted from the plurality of measurement results about each eye and it is used as the measurement result about each eye.

Recently, apparatuses for effecting the aforementioned measurement about both eyes at a time have been devised, but they have many demerits such as high costs and bulkiness in their sizes, and apparatuses which effect measurement about one eye at a time remain the mainstream.

In the conventional ophthalmologic apparatus for effecting measurement about one eye at a time as described above, when many patients are to be continuously measured for a long time, whether the other eye (the eye not under examination) than the eye under examination of a patient being measured has already been measured may sometimes become unknown thus, in spite of the eye not under examination having already been measured, there has been a case where measurement is effected again to cause the waste of time and the pain of the patient. There have also been cases where although the eye not Under examination has not yet been measured, the examiner thinks that it has been measured, and forgets to measure it.

SUMMARY OF THE INVENTION

In view of the above-described circumstances, the present invention has as a first object thereof the provision of an ophthalmologic apparatus in which an operator can grasp the number of times of measurement effected about each of the eye being examined and the eye being not examined.

Also, in many of the conventional ophthalmologic apparatuses for effecting measurement about one eye at a time as described above, an operator and a patient face each other with the ophthalmologic apparatus interposed therebetween. At this time, the patient's face becomes invisible to the operator because the ophthalmologic apparatus is large. In the ophthalmologic apparatus, a monitor for displaying the outer portion of the eye being examined is provided on the operator side, and on this monitor, for example, R is displayed if the eye under examination being measured is the right eye and for example, L is displayed if the eye under examination being measured is the left eye so that the operator can grasp which of the right and left eyes the eye under examination being measured is. However, even when which of the right and left eyes the eye under examination being measured is becomes known, it is difficult to immediately know in which direction the ophthalmic apparatus should be moved to measure the eye not under examination unless the operator becomes experienced.

So, the present invention has as a second object thereof the provision of an ophthalmologic apparatus which makes it easy to immediately know in which direction the ophthalmologic apparatus should be moved to measure the eye not under examination.

To achieve the above objects, according to the present invention, an ophthalmologic apparatus provided with a measuring device for measuring an eye being examined, and a display for displaying the result of the measurement by said measuring device can have:

counting means for counting the number of times of measurement of said eye being examined with respect to each of the right and left eyes; and display control means for causing said display to display the number of times of measurement of each of the right and left eyes counted by said counting means.

Also, the ophthalmologic apparatus can be provided with:

discriminating means for discriminating whether one eye under examination being measured by said measuring device is the left eye or the right eye; and a display for displaying a mark corresponding to the direction toward the other eye under examination to be measured next by said measuring device, on the basis of the result the discrimination by said discriminating means.

In the ophthalmologic apparatus provided with the measuring device for measuring the eye being examined, and the display for displaying the result of the measurement by said measuring device, the number of times of measurement of said eye being examined is counted with respect to each of the left and right eyes by said counting means. The counted number of times of measurement of each of the left and right eyes is displayed on said display by the display control means.

Also, the counted number of times of measurement of the left eye is displayed on the right of the screen of said display device as it faces to the operator, and the counted number of times of measurement of the right eye is displayed on the left of the screen of said display as it faces to the operator.

Further, the number of times of measurement of one of the left and right eyes which is being examined and the number of times of measurement of the other of the left and right eyes which is being examined are displayed in different display forms on said display by display form control means.

Furthermore, the counted frequencies of measurement of the left and right eyes are compared with a predetermined value by comparing means. As a result of this comparison, it is discriminated by the discriminating means that said frequencies of measurement of the left and right eyes have exceeded said predetermined value.

Still further, a first mark indicating that said eye being examined is the right eye and a second mark indicating that said eye being examined is the left eye are displayed on said display by said display control means, and said frequencies of measurement are displayed on said display correspondingly to said first mark and said second mark.

Yet still further, an eye under examination is measured by the measuring device, and whether one eye under examination being measured is the left eye or the right eye is discriminated by the discriminating means. On the basis of the result of the discrimination, a mark corresponding to the direction toward the other eye under examination being measured by said measuring device is displayed.

DESCRIPTION OF THE PREFERRED EMBODIMENTS

An embodiment of the present invention as it is applied to an eye refractometer will hereinafter be described.

Figure 1:
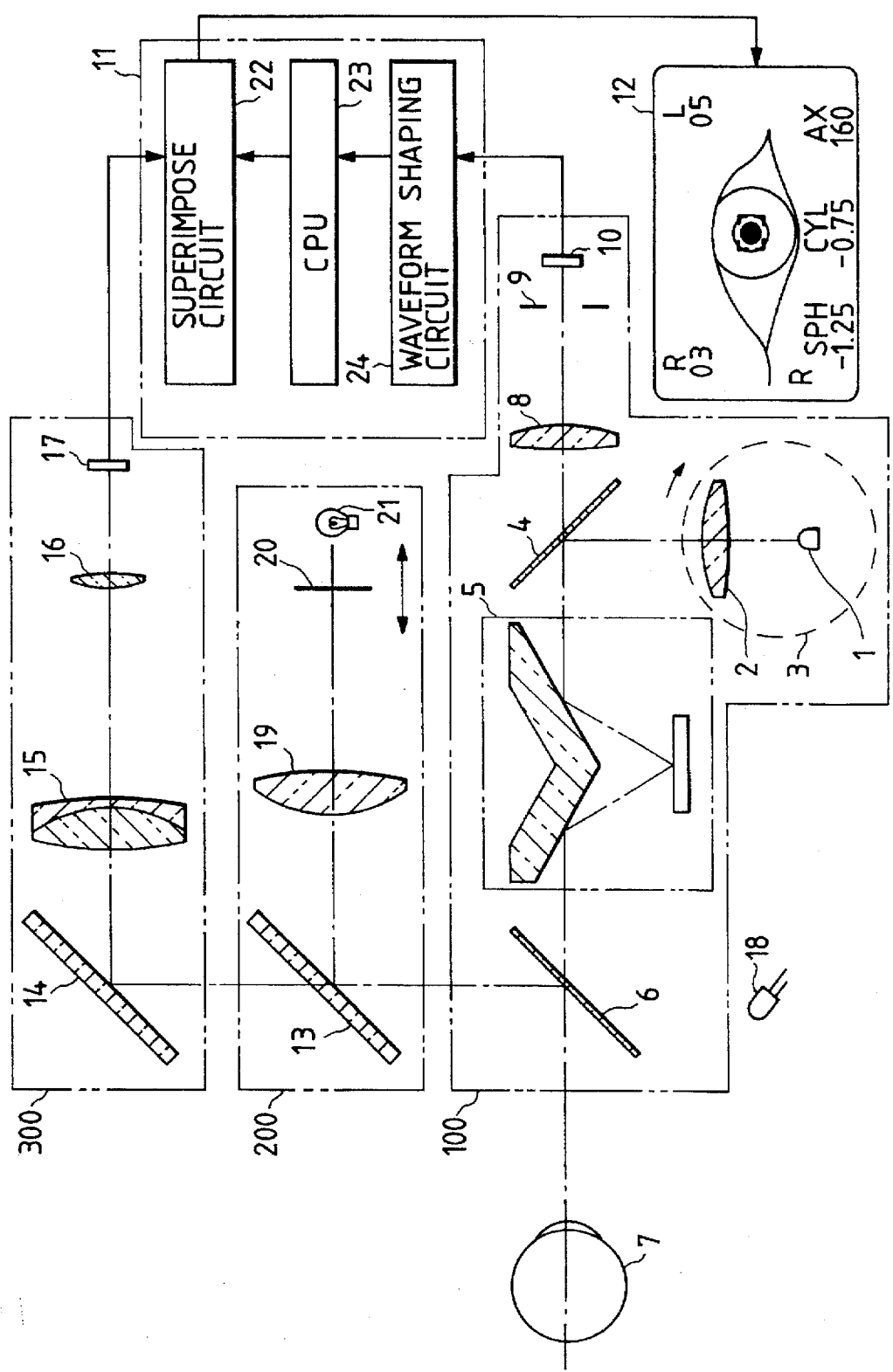
FIG. 1 is an illustration of an example of the construction of an eye refractometer which is an embodiment of the present invention.

FIG. 1 is a schematic illustration of the optical system of an eye refractometer to which the present invention is applied.

This eye refractometer is based on so-called retinoscopy and is described in detail in applicant's Japanese Patent Application Laid-Open No. 55-86437. Retinoscopy is a technique whereby light moving in one direction enters the pupil of an eye being examined and the movement of the reflected light from the fundus of the eye on the pupil is observed to thereby measure the refractive power of the eye being examined.

This eye refractometer is comprised of a measurement and alignment detecting optical system 100, an eye-fixing-target optical system 200 and an observation optical system 300.

The measurement and alignment detecting optical system 100 will first be described.

A measurement light beam emitted from a measuring infrared light source 1 passes through a condenser lens 2, is converted into a slit-like light beam by a rotatable drum 3 having a slit-like opening and rotated, for example, in the direction of arrow in FIG. 1, arrives at an eye 7 being examined through a beam splitter 4 and an image rotator 5 and via a dichroic mirror 6 transmitting infrared light therethrough and reflecting visible light, and scans the fundus of the eye being examined.

The image rotator 5 is being rotated about the optical axis of the measuring light beam by a driving device, not shown, so that scanning light suitable also for the measurement of astigmatism may be obtained.

The reflected light from the eye being examined again passes through the dichroic mirror 6, the image rotator 5 and the beam splitter 4 and through a relay lens 8 and a slit-like stop 9 to a light receiving element 10 for the measurement of eye refractive power and for the detection of alignment.

Figure 2:
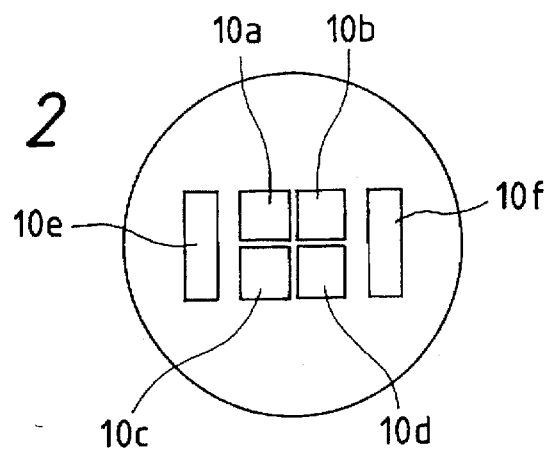
FIG. 2 is an illustration of the construction of a light receiving element.

On the light receiving element 10, as shown in FIG. 2, there are centrally disposed four-division photodiodes 10a, 10b, 10c and 10d for the detection of alignment, and are disposed two photodiodes 10e and 10f for the measurement of eye refractive power outside thereof.

The four-division photodiodes 10a, 10b, 10c and 10d receive as an input the reflected light from the cornea of the eye being examined included in the reflected light from the eye being examined, and effects outputting in conformity with this input. As the ratios of the magnitudes of the outputs from these photodiodes 10a, 10b, 10c and 10d become equal, it can be regarded that the state of alignment is good and the eye being examined and the eye refractometer are at regular position. This method is described in detail in applicant's Japanese Patent Application Laid-Open No. 55-52730.

The reflected light from the fundus of the eye being examined is inputted to the two photodiodes 10e and 10f, from which outputting conforming to the input is done. This output is shaped through a waveform shaping circuit 24 so that an analog waveform may be readily digitally processed, and is inputted to a central processing unit (CPU) 23. For example, when the ratios of the magnitudes of the outputs from the photodiodes 10a, 10b, 10c and 10d become equal and it is judged that the state of alignment is good, eye refractive power data such as the spherical power, cylindrical power and cylindrical axis of the eye being examined are calculated in the CPU 23, and the eye refractive power data are superimposed on the image of the eye being examined picked up by the observation optical system 300 which will be described later, through a superimpose circuit 22, and are displayed on a monitor 12. Also, for example, a measurement switch, not shown, is prepared and when this measurement switch is depressed by an operator, the eye refractive power data may be calculated in the CPU 23, and the eye refractive power data may be superimposed on the image of the eye being examined picked up by the observation optical system 300 which will be described later, through the superimpose circuit 22, and may be displayed on the monitor 12.

Figure 8:
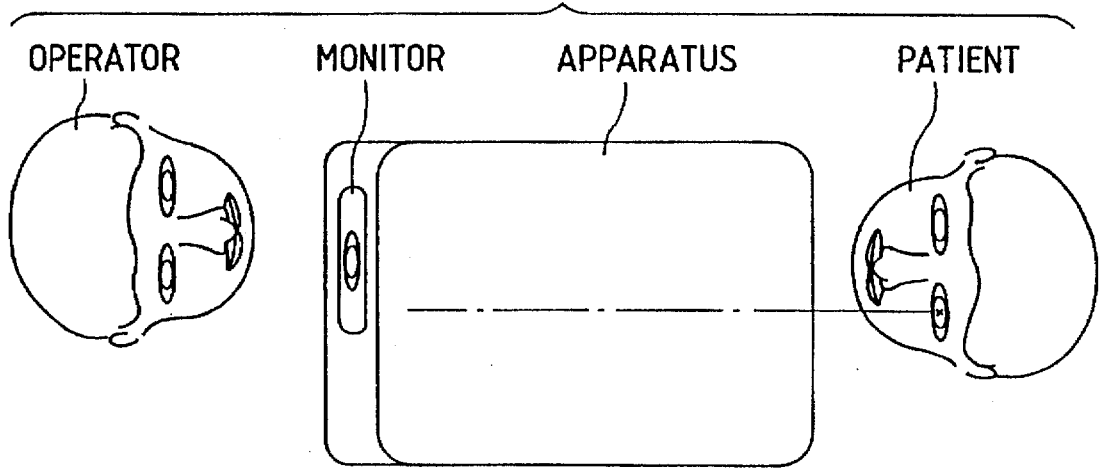
FIG. 8 is an illustration of the positional relations according to the present invention among an operator, a patient, an ophthalmologic apparatus and the monitor of the ophthalmologic apparatus.

The CPU 23 counts the frequencies of measurement of the eye refractive power data of the left and right eyes and displays the frequencies of measurement on the monitor 12 through the superimpose circuit 22. At this time, the positional relations among the operator, the patient, the ophthalmologic apparatus and the monitor are such as shown in FIG. 8 and therefore, the number of times of measurement of the patient's left eye may be displayed on the right of the monitor as it faces to the operator and the number of times of measurement of the patient's right eye may be displayed on the left of the monitor as it faces to the operator. Also, design may be made such that when the frequencies of measurement of the eye refractive power data of the left and right eyes both exceed a predetermined frequency, the CPU 23 outputs the calculated eye refractive power data to a printing apparatus, not shown. On the display screen of the monitor 12 of FIG. 1, it is shown that spherical power (SPH) is −1.25, cylindrical power (CYL) is −0.75 and cylindrical axis (AX) is 160. These measurement values are measurement values measured latest for the patient's eye now under examination. Also, as will be described later, whether the eye under examination is the right eye or the left eye is detected and it is indicated by R that the eye under examination is the right eye. Further, it is indicated that the number of times of measurement of the right eye is three times and the number of times of measurement of the left eye is five times.

Figure 3A:
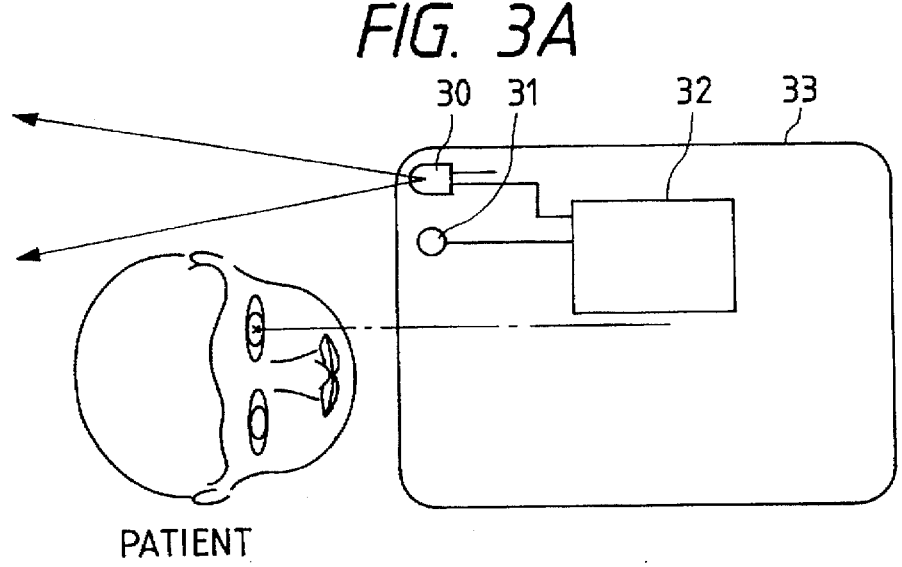
FIGS. 3A and 3B are illustrations of a mechanism for detecting which of the left and right eyes the eye being examined is.
Figure 3B:
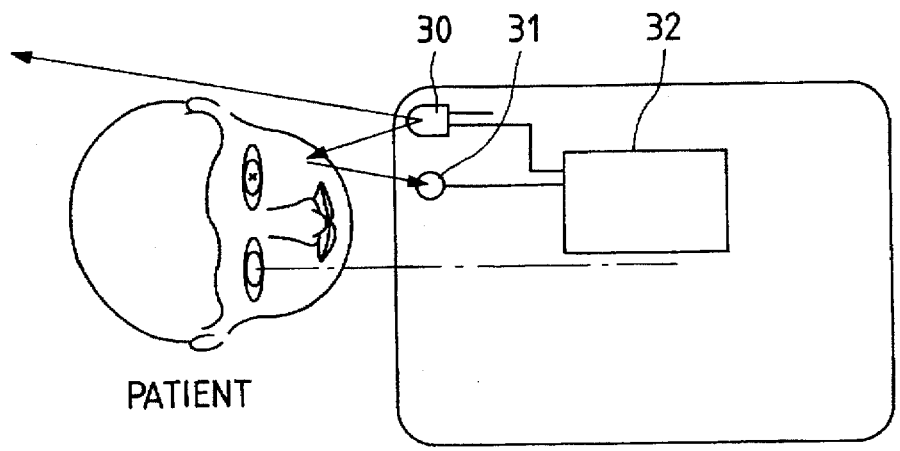

A method of detecting whether the eye under examination is the right eye or the left eye will now be described with reference to FIGS. 3A and 3B. FIGS. 3A and 3B are illustrations of left and right eyes detecting means.

FIG. 3A shows a case where the eye under examination is the left eye. Infrared light is emitted from a light source 30, but the emitted infrared light does not impinge on the patient's face and the reflected light from the patient's face is 0 or little. Therefore, the output of a light receiving element 31 which receives the infrared light is 0 or small. In such a case, discriminating means 32 discriminates that the eye under examination is the left eye.

FIG. 3B shows a case where the eye under examination is the right eye. When infrared light is emitted from the light source 30, the emitted infrared light impinges on the patient's face and the reflected light from the patient's face is much. Therefore, the output of the light receiving element 31 which receives the infrared light is great. In such a case, the discriminating means 32 discriminates that the eye under examination is the right eye.

Design may be made such that the function of this discriminating means 32 is performed by the CPU 23 shown in FIG. 1. Design can be made such that in order that L may be displayed on the monitor 12 when it is discriminated by the CPU 23 that the eye under examination is the left eye, and R may be displayed on the monitor 12 when it is discriminated by the CPU 23 that the eye under examination is the right eye, R or L is superimposed by the superimpose circuit 22 and is displayed on the monitor 12 with the image of the eye under examination.

Figure 7:
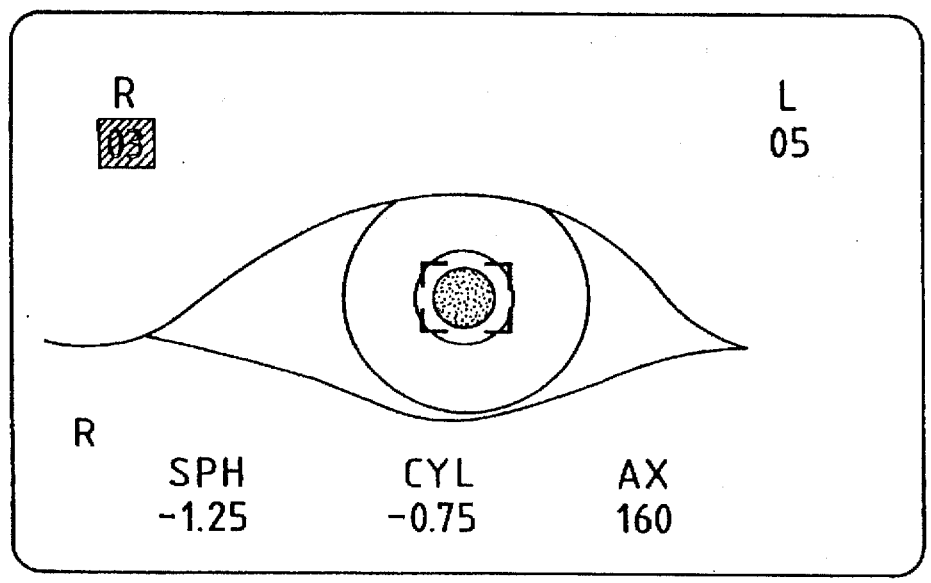
FIG. 7 is an illustration of the display screen of the monitor according to the present invention.

The number of times of measurement of the eye judged to be the eye under examination by the left and right eyes detecting means of FIGS. 3A and 3B and the number of times of measurement of the eye not judged to be the eye now under examination by the left and right eyes detecting means of FIGS. 3A and 3B may be displayed in different display forms on the monitor 12, as shown in FIG. 7. In FIG. 7, the eye under examination is the right eye and therefore, the number of times of measurement of the right eye is emphatically displayed.

Figure 4:
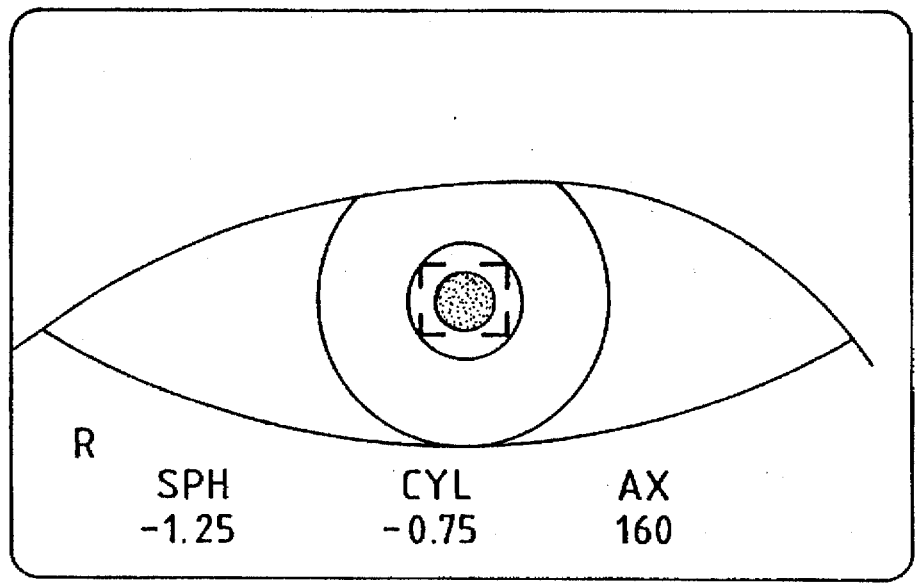
FIG. 4 is an illustration of the display screen of a monitor according to the prior art.
Figure 5:
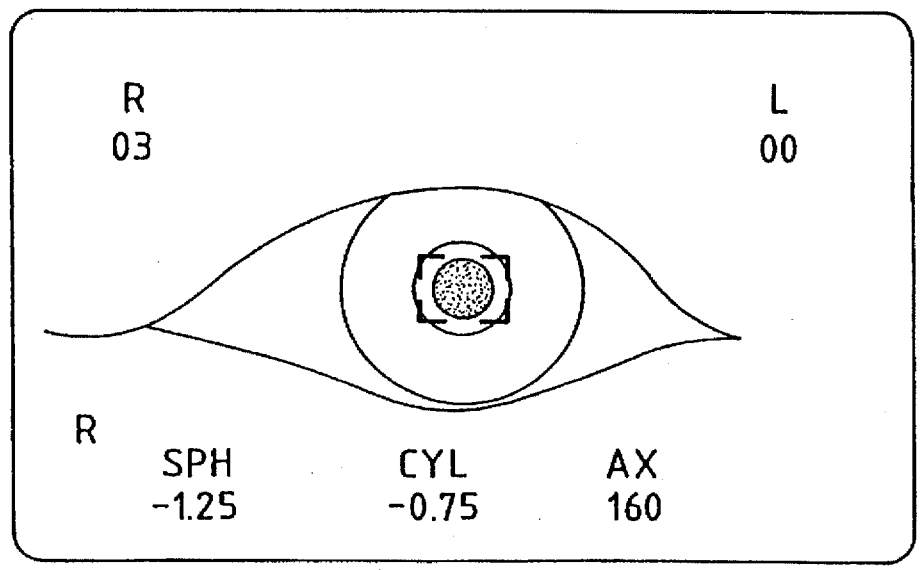
FIG. 5 is an illustration of the display screen of a monitor according to the present invention.
Figure 6:
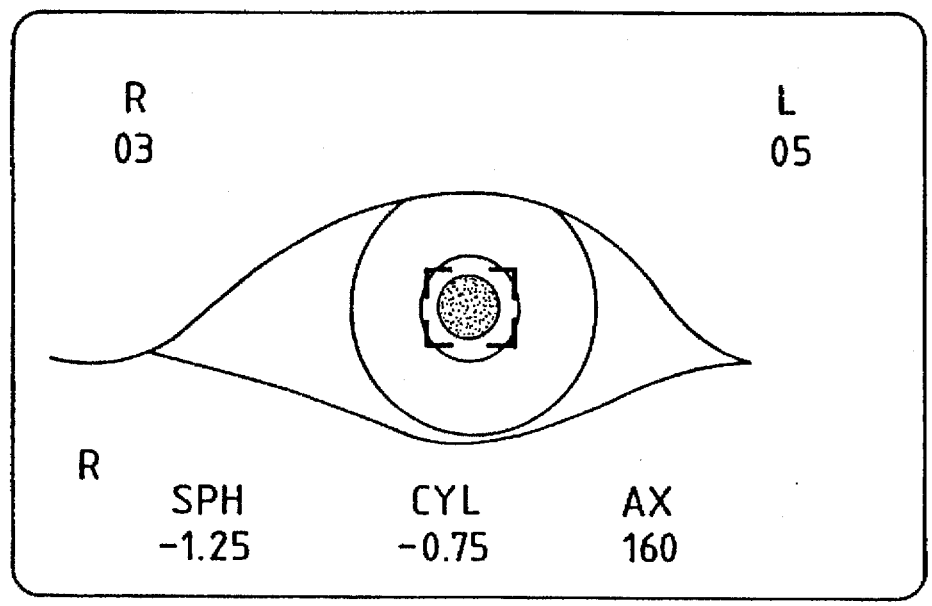
FIG. 6 is an illustration of the display screen of the monitor according to the present invention.

An example of the display screen of the monitor 12 according to the prior art is shown in FIG. 4, and examples of the display screen of the monitor 12 according to the present invention are shown in FIGS. 5 and 6. In FIG. 4, R indicating that the eye under examination is the right eye is displayed and it is displayed that spherical power (SPH), cylindrical power (CYL) and cylindrical axis (AX) which are eye refractive power data are −1.25, −0.75 and 160, respectively, but the frequencies of measurement of the left and right eyes are not displayed. In FIG. 5, R indicating that the eye under examination is the right eye is displayed and eye refractive power data are also displayed as in FIG. 4. Moreover, it is displayed on the left of the display screen that the right eye has already been measured three times, and it is displayed on the right of the display screen that the left eye is not yet measured. In FIG. 6, R indicating that the eye under examination is the right eye is displayed and eye refractive power data are also displayed as in FIG. 4. Moreover, it is displayed on the left of the display screen that the right eye has already been measured three times, and it is displayed on the right of the display screen that the left eye has already been measured five times. The eye refractive power data displayed in FIGS. 5 and 6 are measurement values measured latest for the patient now.

Figure 9:
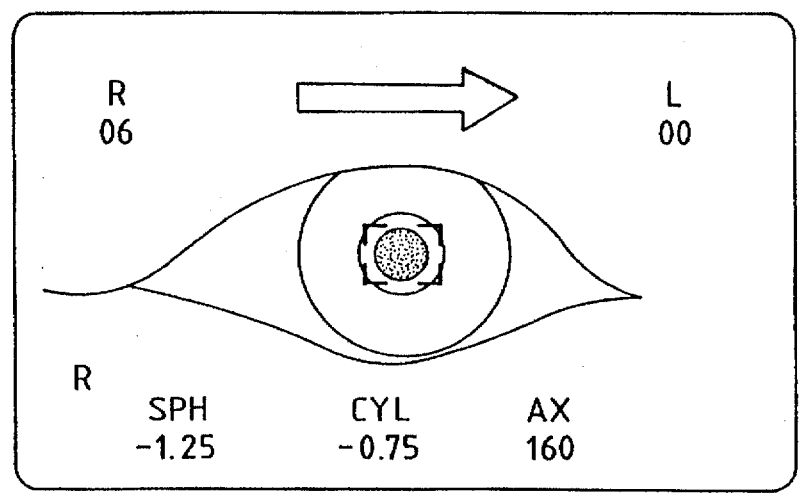
FIG. 9 is an illustration of the display screen of the monitor on which an arrow according to the present invention is displayed.

Further, the screen of the monitor of the eye refractometer for displaying a mark (arrow) indicative of the direction toward an eye which is not the eye under examination being measured (an eye not under examination) will be described with reference to FIG. 9. In FIG. 9, R indicating that the eye under examination is the right eye is displayed and it is displayed that spherical power (SPH), cylindrical power (CYL) and cylindrical axis (AX) which are eye refractive power data are −1.25, −0.75 and 160, respectively.

Moreover, it is displayed on the left of the display screen that the right eye has already been measured six times, and it is displayed on the right of the display screen that the left eye is not yet measured. Also, the direction in which the patient's left eye to be measured next is is indicated by an arrow and therefore, the operator can move the eye refractometer in the direction of arrow. Thus, it does not happen that the operator errs in judging in which direction the eye refractometer should be moved to adjust the position of the eye refractometer to the eye under examination to be measured next.

The above-mentioned arrow, as will be described later, may be designed to be displayed when the number of times of measurement of the eye under examination has reached a predetermined value (a predetermined number). Also, the arrow may be displayed when the number of times of measurement of the eye under examination has reached the predetermined number and the eye not under examination is not yet measured. Design may also be made such that an arrow indicative of the direction toward the eye not under examination is normally displayed and when the number of times of measurement of the eye under examination has reached the predetermined number, emphatic display such as flickering display is effected to attract the operator's attention. Further, sound generating means such as a buzzer may be used to inform the operator by sound that the number of times of measurement of the eye under examination has reached the predetermined number. Further, design may be made such that the result of measurement (eye refractive power data for the number of times of measurement) is outputted to the printing apparatus, not shown, at a point of time whereat the number of times of measurement of both eyes of the patient have reached the predetermined number.

The case where as described above, the arrow is displayed when the number of times of measurement of the eye under examination has reached the predetermined number will hereinafter be described with reference to the flow chart of FIG. 10.

Figure 10:
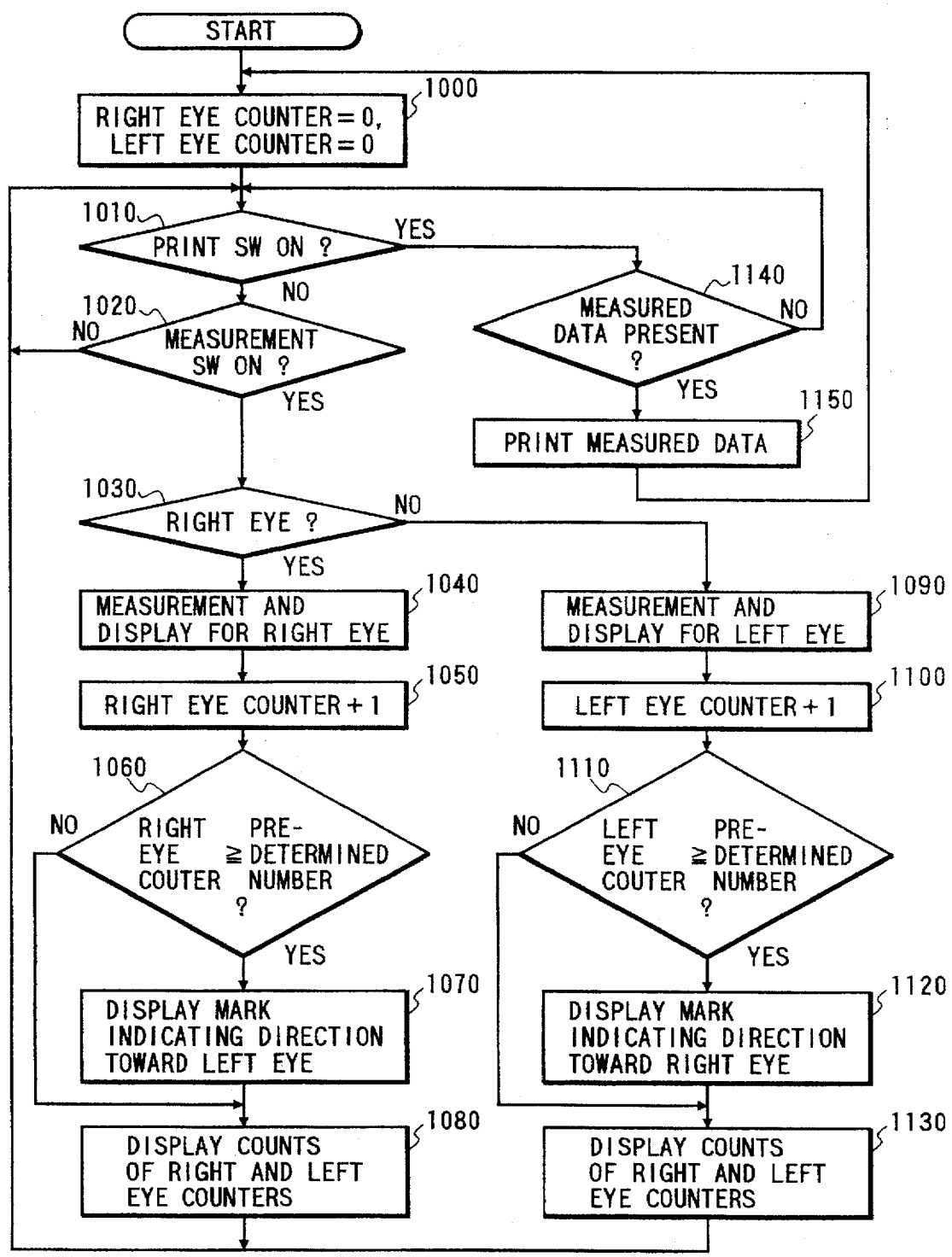
FIG. 10 is a flow chart showing an example of the arrow displaying operation according to the present invention.

In FIG. 10, it is to be understood that a print switch (print SW) is provided and when this print SW is depressed by the operator, the result of measurement is outputted to the printing apparatus, not shown. Also, it is to be understood that a measurement switch (measurement SW) is provided and when this measurement SW is depressed by the operator, the measurement of the eye under examination is effected. Further, the number of times of measurement of the left and right eyes are counted by the use of a left eye counter and a right eye counter, respectively. The setting of the display timing for arrows as shown in FIG. 10 is effected by the CPU 23 in FIG. 1. The directions (shapes) of the arrows are determined by the CPU 23 on the result of the discrimination by the aforedescribed left and right eyes detecting means (see FIGS. 3A and 3B). The display of the arrows on the monitor 12 is effected by the superimposed circuit 22 in FIG. 1.

Now, FIG. 10 will be described hereinafter. The CPU 23 renders the values of the right eye counter and the left eye counter into 0 (step 1000). Next, whether the print SW has been depressed by the operator is judged (step 1010). If it is judged that the print SW has been depressed, advance is made to a step 1140, where whether measurement data are present is judged. If it is judged that the measurement data are absent, nothing is done and return is made to the step 1010. If it is judged that the measurement data are present, the measurement data are outputted to the printing apparatus, not shown, (step 1150), and return is made to the step 1000. If at the step 1010, it is judged that the print SW has not been depressed, advance is made to a step 1020, where whether the measurement SW has been depressed is judged. If at the step 1020, it is judged that the measurement SW has not been depressed, return is made to the step 1010. If at the step 1020, it is judged that the measurement SW has been depressed, whether the eye under examination is the right eye is judged at a step 1030. If at the step 1030, it is judged that the eye under examination is the right eye, the measurement of the eye under examination and the display of the result of the measurement and of the eye under examination are effected (step 1040), and 1 is added to the value of the right eye counter (step 1050). Subsequently, the value of the right eye counter is compared with the predetermined number (step 1060), and if the value of the right eye counter is equal to or greater than the predetermined number, advance is made to a step 1070, where the display of a mark (arrow) indicative of the direction toward the left eye is effected. Thereafter, at a step 1080, the values of the right eye counter and the left eye counter are displayed on the monitor 12. If at the step 1060, the value of the right eye counter is less than the predetermined number, advance is made to the step 1080. From the step 1080, return is made to the step 1010. If at the step 1030, it is judged that the eye under examination is not the right eye, the measurement of the eye under examination and the display of the result of the measurement and of the eye under examination are effected (step 1090), and 1 is added to the value of the left eye counter (step 1100). Subsequently, the value of the left eye counter is compared with the predetermined number (step 1110), and if the value of the left eye counter is equal to or greater than the predetermined number, advance is made to a step 1120, where the display of a mark (arrow) indicative of the direction toward the right eye is effected. Thereafter, at a step 1130, the values of the right eye counter and the left eye counter are displayed on the monitor 12. If at the step 1110, the value of the left eye counter is less than the predetermined number, advance is made to the step 1130. From the step 1130, return is made to the step 1010.

The eye-fixing-target optical system 200 will now be described.

A light source 21 illuminates an eye fixing target 20, and the light beam from the eye fixing target 20 is made into a substantially parallel light beam by a collimator lens 19. This light beam is reflected by a cold mirror 13 and is further reflected by the dichroic mirror 6 and arrives at the eye 7 under examination, which fixates at the eye fixing target 20. The eye fixing target 20 is movable in the direction of the optical axis and is placed each time at a position whereat the eye under examination can fixate in its unadjusted state.

Further, the observation optical system 300 will hereinafter be described.

A light beam emitted from an infrared light source 18 for illuminating the outer portion of the eye under examination illuminates the eye under examination and the portion around the eye under examination. This light beam illuminating not only the eye under examination but also the portion around it is partly reflected by the dichroic mirror 6 (the dichroic mirror 6 transmits infrared light therethrough and reflects visible light, but reflects part of the infrared light). The reflected light beam is transmitted through the cold mirror 13, is deflected by a mirror 14 and enters an image pickup device 17 via a relay lens 15 and an imaging lens 16. An image formed on the image pickup device 17 is picked up by the image pickup device 17, and is superposed on a mark or the like to which the central portion of the eye should be adjusted, through the superimpose circuit 22, and is displayed on the monitor 12.

Lastly, an example of the operation in the present invention will be described. The image of the eye fixing target is entered into the eye under examination by the eye-fixing-target optical system 200, and the eye under examination fixates at the eye fixing target. The patient's face including the outer portion of the patient's eye under examination is image-picked up by the observation optical system 300, and a mark to which the center of the eye under examination should be adjusted is superimposed on the picked-up image and is displayed on the monitor. When the eye to be measured is the right eye, the operator moves the ophthalmologic apparatus so as to superposed the right eye on the aforementioned mark. The operator adjusts the center of the eye under examination to the mark. The alignment state is detected by the measurement and alignment detecting optical system 100, and when a position good in alignment is assumed, the operator measures eye refractive power data. Also, the measurement of eye refractive power data may be effected by the measurement switch being depressed by the operator. The measured eye refractive power data are superimposed on the image of the eye under examination and are displayed on the monitor. At this time, the number of times of measurement of the eye refractive power data of the left and right eyes are displayed on the monitor. The operator can grasp the number of times of measurement of the eye refractive power data of the left and right eyes by the number of times of measurement displayed on the monitor and therefore, it does not happen that the operator forgets to measure or measures too much. Also, when for example, the number of times of measurement of the eye refractive power data of the left eye exceeds the predetermined number, an arrow indicative of the direction toward the right eye is displayed. When the number of times of measurement of the eye refractive power data of the right eye exceeds the predetermined number, an arrow indicative of the direction toward the left eye is displayed. The operator can know the direction in which the eye not under examination is by the arrow displayed on the monitor and therefore, it does not happen that the operator mistakes in which direction he should move the refractometer to align the eye refractometer with the eye to be measured next. Further, when for example, the number of times of measurement of the eye refractive power data of the left and right eyes both exceed the predetermined number, the eye refractive power data of the left and right eyes so far measured in succession are outputted from the printing apparatus.

According to the present invention, there can be provided an ophthalmologic apparatus by which the operator can grasp the number of times of measurement effected about each of the eye under examination and the eye not under examination (the eye which is not the eye under examination). Thereby, the operator can prevent himself from forgetting to measure or from measuring too much, thus enhancing the efficiency of measurement.

Also, according to the present invention, there can be provided an ophthalmologic apparatus in which the direction in which the ophthalmologic apparatus should be moved to measure the eye not under examination is indicated by an arrow and can be intuitionally easily known. Thereby, the operator can immediately recognize in which direction the ophthalmologic apparatus should be moved, thus enhancing the efficiency of measurement.

What is claimed is:

1. An ophthalmologic apparatus comprising:
   a measuring device for measuring an eye being examined;
   a display for displaying the result of the measurement by said measuring device;
   a counter for counting the number of times of measurement of said eye being examined with respect to the right and left eyes; and a display control device for causing said display to display the number of times of measurement of each of the right and left eyes counted by said counter.

2. An ophthalmologic apparatus according to claim 1, wherein said display control device causes the number of times of measurement of the patient's left eye counted by said counter to be displayed on the right of the screen of said display to the operator, and causes the number of times of measurement of the patient's right eye counted by said counter to be displayed on the left of the screen of said display to the operator.

3. An ophthalmologic apparatus according to claim 1, wherein said display control device has a display form control device for causing said display to display the number of times of measurement of one of the right and left eyes and the number of times of measurement of the other of the right and left eyes in different display forms.

4. An ophthalmologic apparatus according to claim 1, further comprising:
   a comparator for comparing the number of times of measurement of the right and left eyes counted by said counter with a predetermined value; and
   a discriminator for discriminating as a result of the comparison by said comparator that the number of times of measurement of the right and left eyes have exceeded said predetermined value.

5. An ophthalmologic apparatus according to claim 1, wherein said display control device causes said display to display a first mark indicating that said eye being examined is the right eye and a second mark indicating that said eye being examined is the left eye, and causes said display to display said number of times of measurement of each of the right and left eyes correspondingly to said first mark and said second mark.

6. An ophthalmologic apparatus comprising:
   a measuring apparatus for measuring an eye under examination;
   a discriminator for discriminating whether one eye under examination being measured by said measuring device is the left eye or the right eye; and
   a display for displaying a mark indicative of the direction toward the other eye under examination to be measured next by said measuring device, on the basis of the result of the discrimination by said discriminator.

* * * * *